United States Patent [19]

Shansky

[11] 4,097,589

[45] Jun. 27, 1978

[54] NAIL POLISH

[75] Inventor: Albert Shansky, Norwalk, Conn.

[73] Assignee: Del Laboratories, Inc., Farmingdale, N.Y.

[21] Appl. No.: 814,439

[22] Filed: Jul. 11, 1977

Related U.S. Application Data

[63] Continuation-in-part of Ser. No. 654,153, Feb. 2, 1976, abandoned.

[51] Int. Cl.$^2$ ............................................. A61K 7/043
[52] U.S. Cl. ...................................... 424/61; 424/358
[58] Field of Search ............................................ 424/61

[56] References Cited

U.S. PATENT DOCUMENTS

| 3,234,097 | 2/1966 | Loughran et al. | 424/61 |
| 3,301,760 | 1/1967 | Jewel | 424/61 |
| 3,342,686 | 9/1967 | Jewel | 424/61 |
| 3,423,367 | 1/1969 | Merizan et al. | 260/66 |
| 3,483,289 | 12/1969 | Michaelson et al. | 424/61 |
| 3,864,294 | 2/1975 | Busch, Jr. | 260/28.5 A |

FOREIGN PATENT DOCUMENTS

| 832,034 | 1/1970 | Canada | 424/61 |
| 1,267,983 | 6/1961 | France | 424/61 |
| 724,041 | 2/1955 | United Kingdom | 424/61 |

*Primary Examiner*—Dale R. Ore
*Attorney, Agent, or Firm*—Kirschstein, Kirschstein, Ottinger, Frank & Cobrin

[57] ABSTRACT

A liquid nail polish which imparts improved flexural strength to the human nail and inhibits splitting when applied thereto as a coating. The nail polish formulation is characterized by the inclusion therein, as a dissolved component, of a small but effective amount of a terpolymer comprising a copolyamide consisting essentially of recurring units of equimolecular proportions of caprolactam, laurolactam and hexamethylene diamine adipate. Typically, said terpolymer is first dissolved in a mixture of trichloroethane and ethyl alcohol, and this liquid solution is added in a small quantity to a stock liquid nail polish formulation so that a final formulation containing a small but effective amount of said dissolved terpolymer is produced, e.g. a formulation containing in the range of about 0.001 to 0.1% by weight of said dissolved terpolymer.

2 Claims, No Drawings

NAIL POLISH

CROSS-REFERENCE TO RELATED APPLICATION

The present application is a continuation-in-part of application Ser. No. 654,153 filed Feb. 2, 1976 for NAIL POLISH, now abandoned.

BACKGROUND OF THE INVENTION

1. Field of the Invention

This invention relates to liquid nail polish formulations which are applied to human nails as a coating and allowed to dry, leaving a film of solid material on the nails, generally for cosmetic purposes.

2. Description of the Prior Art

U.S. Pat. Nos. 3,301,760 and 3,342,686 describe the inclusion of nylon fibers in a liquid nail polish formulation to repair broken or cracked fingernails. British Pat. No. 724,041 relates to the inclusion of nylon in nail polish in amounts of 1 to 4 percent of the weight of the total solids in the polish. U.S. Pat. No. 3,234,097 describes a fingernail enamel, i.e. a nail polish, containing finely ground chlorite mineral.

Numerous types of nail polish are sold commercially, generally, however, in small quantities, which contain a solid in the formulation, typically in suspension, in order to enhance the attractive appearance of or to provide a novelty effect to the final coated nail or to supply a special additional characteristic; however, the basic market for nail polish formulations, in general, is for a totally liquid nail polish which when applied and allowed to dry gives the nails an attractive uniform coating of the desired color or hue.

Thus, typical commercial nail polish formulations contain a solvent or mixture of solvents which are usually organic solvents such as toluol, lower aliphatic acetates, lower aliphatic alcohols, etc; plasticizers such as camphor, dibutyl phthalate, tricresyl phosphate, castor oil, and diethyl phthalate; a film former, usually nitrocellulose or the like; and a modifying resin such as melamine-formaldehyde, ureaformaldehyde, an alkyd resin of the pentaerythritol series, sucrose benzoate, acrylics, or toluene-sulfonamide-formaldehyde resin. Such formulations also usually contain coloring agents such as a dye or the like, odor-modifying agents such as a perfume base, etc., and the final product is a colored uniform liquid formulation devoid of solid content.

SUMMARY OF THE INVENTION

1. Purpose of the Invention

This invention seeks to provide an improved liquid nail polish formulation.

This invention also seeks to provide such a formulation in which a special copolyamide terpolymer is dissolved in the formulation.

Additionally, the invention seeks to provide a liquid formulation which, when applied as a coating to the human nail and allowed to dry, will leave a coating that imparts high flexural strength to the nail and inhibits splitting of the nail.

These and other objects and advantages of the present invention will become evident from the description which follows.

2. Brief Description of the Invention

According to the present invention, it has been discovered that a small but effective amount of a special terpolymer, when included in a liquid nail polish formulation as an integral dissolved component of such formulation, substantially improves the characteristics of said formulation after it has been applied to a nail and permitted to dry thereon as a nail polish film.

Specifically, the terpolymer is a copolyamide consisting essentially of equimolecular proportions of recurring units of caprolactam, laurolactam and hexamethylene diamine adipate. When this special terpolymer is incorporated as a dissolved component in a liquid nail polish formulation and applied to a nail, the ensuing nail polish film substantially increases the flexural strength of the underlying nail and the resistance of such nail to splitting. In addition to improving the physical characteristics of the underlying nail, the special terpolymer performing in an applied coating acts to some extent as a plasticizer, and the resulting coating on the nail is uniform in texture and thickness and has a pleasing effect on the eye.

It has been determined that optimum results are obtained when the special terpolymer is present in the liquid nail polish as a dissolved component if the said terpolymer is employed in an amount ranging from about 0.001 to about 0.1% by weight of the liquid nail polish composition. Moreover, pursuant to the present invention said special terpolymer is provided in a particular specific physical form prior to solvation, namely, in an extremely small particle size below 80 microns. Any larger starting size, i.e. size prior to dissolution, prevents the attainment of the present invention due to the inability of the special terpolymer to be fully dissolved.

In accordance with this invention, the said special terpolymer initially is dissolved in a solvent composed of trichloroethane and ethyl alcohol, said terpolymer prior to solvation having a particle size of less than 80 microns, e.g. about 10 to about 70 microns. A small amount of the special terpolymer, typically about 1% by weight of the total solution, is completely solubilized in said mixture of trichloroethane and ethyl alcohol. Then a small amount of the solution containing the dissolved special terpolymer is added to a standard, i.e. stock, liquid nail polish formulation. In most instances the amount by weight of the solution of the special terpolymer added is less than 1% of the total weight of the stock liquid nail polish formulation.

The initial liquid solution of the special terpolymer can be added to a stock nail polish formulation by spraying the same into a powder blender in which particles of a modifying resin, namely, toluene-sulfonamide-formaldehyde resin, are being tumbled. Said liquid solution is sprayed into the powder blender as a fine atomizing mist to obtain a uniform dispersion of the liquid over and onto the powdered resin. The material in the powder blender is tumbled until uniform and then is passed into a pulverizer such as a Mikro-pulverizer and is ground to the micron size range which is the finest setting on the pulverizer. The ensuing fine powder then is added to the balance of the standard nail polish formulation in the requisite proportion to yield a liquid nail polish containing said dissolved special terpolymer in a small but effective amount.

The nail polish formulation of the present invention provides several salient advantages. As mentioned supra, a viable and substantial increase in the flexural strength of the nails is attained. Other strength parameters such as tensile strength and impact strength of the nails also are increased. Thus, the resistance of the nails to splitting is increased.

The invention accordingly consists in the composition as hereinafter described and of which the scope of application will be indicated in the appended claims.

DETAILED DESCRIPTION OF THE PREFERRED EMBODIMENTS

More Detailed Description of the Prior Art

Solvent systems were formulated based on British Pat. No. 724,041. To these solvent systems were added incremental quantities of various prilled nylons, from 0.01 to 1% by weight, with continuous rapid stirring and no resulting solubility of the nylon. These solvents were then refluxed with 0.1% concentrate of each nylon copolymer for 30 minutes each, without resulting solubility.

The nylon copolymers used were Platamid, Elvamide 8063 and Elvamide 8062. The Elvamide series of nylon copolymers are furnished by duPont Corporation in the form of nugget-sized particles of 1 mm. × 1 mm. dimension. These three resins were used individually and separately in each solvent mixture.

Platamid is the special terpolymer mentioned above which is used pursuant to the present invention in an initially very fine particle size for dissolving in a certain mixture of solvents. Platamid is a terpolymer of laurolactam, caprolactam and hexamethylene diamine adipate in which the various monomers, i.e. caprolactam, laurolactam and hexamethylene diamine adipate, are present in equimolecular proportions in recurring units. Said special terpolymer is characterized by several physical characteristics. Thus, it has a melting point of 120° C; its solubility temperature in polyhydric alcohols is: 144° C in ethylene glycol, 143° C in propylene glycol and 181° C in glycerine; it has a specific gravity of 0.835 to 0.861; it is insoluble in 4.2 molar hydrochloric acid from room temperature to boiling and is soluble at room temperature in 90% formic acid; it has a shear sensitivity of 1.5 ($\mu$A at 100 sec$^{-1}$/$\mu$A at 1000 sec$^{-1}$) at 300° C, a water absorption of from 9 to 10% in boiling water, a water absorption of 1.12 in 24 hours (ASTM D-570), an equilibrium with 50% room humidity of 1.97, a water saturation of 6.33, a brittleness temperature of −56° C (ASTM D-764), a hardness of 64.70 on the Shore D-scale (ASTM D-2240), a tensile strength of 7400 lb. in$^{-2}$ (ASTM D-1708); and an elongation at break of 300% (ASTM D-1708).

The three monomers can be copolymerized in the following manner to form said special terpolymer. The hexamethylene diamine adipate is made by reacting hexamethylene diamine with adipic acid in stoichiometric proportions, i.e. in a mole ratio of 1:1. Each of the reactants is dissolved in methanol in equal molecular proportions and mixed. The resulting salt precipitates and is collected. It is dissolved in water and charged to an evaporator where it is concentrated to a liquor containing about 75% by weight of hexamethylene diamine adipate. The concentrated liquor is transferred to a pressure reactor which has been purged of oxygen, e.g. has a nitrogen atmosphere. There then is added an equimolecular quantity of caprolactam. The mixed solution is heated to about 210° C in the closed reactor or until a pressure has been reached of about 17 atmospheres. The pressure in the reactor is maintained while steam is bled and the temperature gradually is increased. Finally the pressure is reduced to atmospheric pressure and the temperature increased to 280° C. Thereupon an equimolecular weight of laurolactam is added. The laurolactam is added at a temperature between 200° C and 280° C. It is mixed with the hexamethylene diamine adipate and the caprolactam. Mixing is continued and the temperature is raised to 300° C–350° C whereupon the three monomers will be copolymerized to create a terpolymer of said three monomers in which the monomers are present as recurring units and is equimolecular proportions. The special terpolymer now is cooled, removed from the vessel, washed, dried and reduced to a powder having a size of less than 80 microns, namely, from about 10 to 70 microns.

The solvent mixtures as disclosed in British Pat. No. 724,041 were as follows:

|  | Solvent Systems | | |
| --- | --- | --- | --- |
|  | 1 | 2 | 3 |
| Methyl alcohol | 14.50 | — | 14.05 |
| Isopropyl alcohol | 20.10 | — | 20.01 |
| N-butyl alcohol | 9.25 | — | 9.25 |
| Ethyl acetate | 17.25 | 42.5 | 17.25 |
| Amyl acetate | 6.30 | 18.5 | 6.05 |
| Diacetone alcohol | 0.20 | — | 0.02 |
| Butyl Cellosolve | 0.70 | — | 0.07 |
| Xylene | — | 3.5 | — |
| Toluene | 28.00 | — | 28.00 |
| Methyl ethyl ketone | 2.50 | 16.0 | 3.05 |
| Butyl acetate | — | 18.5 | — |
| Tetra hydro furfuryl alcohol | — | 1.0 | — |
|  | 98.80 | 100.0 | 97.75 |

Due to the lack of success of this experiment, it was concluded, inter alia, that a solution of dissolved nylon was evidently not effected in the scheme of the British Pat. No. 724,041.

The Present Invention

The various features of the new liquid nail polish and of methods for manufacturing and using the same will now be described in detail.

A liquid nylon intermediate solution was prepared using the special terpolymer in the aforesaid particle size (sub 80$\mu$).

Said special terpolymer was solubilized using a mixed solvent of 20 parts by weight of trichloroethane and 79 parts by weight of ethyl alcohol. The mixed solvent was warmed to a temperature in the range of 50° C to 70° C, specifically about 60° C.

Then one part by weight of said special terpolymer was added to the warmed mixed solvent and the mixture was stirred at 60° C until all of said terpolymer became dissolved. The result was a clear, colorless and freely flowing liquid solution having a specific gravity of 1.08 to 1.11.

To complete the preparation of the present liquid nail polish formulation, 0.50 parts by weight of the clear liquid solution was added to the 99.50 parts by weight of a stock nail polish formulation and the mixture was stirred until uniform. This specifically produced a product with 0.005% of the dissolved special terpolymer; however, in general, formulations containing in the range of about 0.001 to about 0.1% by weight of the dissolved special terpolymer are feasible.

Typical stock nail polish formulations to which the present invention is applicable are as follows:

| Stock Formulation I | |
| --- | --- |
| Component | % By Weight |
| Nitrocellulose | 12.5 |
| Toluene-sulfonamide-formaldehyde resin | 10.0 |

| Stock Formulation I | |
|---|---|
| Component | % By Weight |
| Camphor | 3.0 |
| Dibutyl phthalate | 5.0 |
| Ethyl acetate | 25.0 |
| Butyl acetate | 23.5 |
| Toluene | 20.0 |
| Titanium dioxide | 0.5 |
| Amaranth (C.I.No. 184) | 0.5 |

| Stock Formulation II | |
|---|---|
| Component | Amount By Weight |
| Nitrocellulose | 14.4 |
| Toluene-sulfonamide-formaldehyde resin | 7.2 |
| Dibutyl phthalate | 3.6 |
| Ethyl acetate | 15.2 |
| Butyl acetate | 12.98 |
| Ethyl alcohol | 6.14 |
| Butyl alcohol | 1.06 |
| Toluene | 35.42 |

Said nail polish formulations are characterized by the presence therein of nitrocellulose and a solvent for the nitrocellulose, said solvent being a mixture of ethyl acetate, butyl acetate, toluene and butyl alcohol. There also preferably is employed in the stock nail polish formulation a toluene-sulfonamide-formaldehyde resin which latter may have been simply mixed into the stock nail polish formulation or which may have been blended with the special terpolymer pursuant to the method described earlier herein.

Laboratory tests were made comparing a stock nail polish formulation with and without the dissolved special terpolymer, with respect to the effect on the physical properties of human fingernails. The tests showed that the special terpolymer-containing formulations produced flexural strength values significantly higher than the formulations without the special terpolymer. In 32 pairs of samples tested, the nails with the special terpolymer-containing formulation applied as two coatings were 18.9% stronger (higher flexural strength value) than the nails with the formulation without dissolved special terpolymer applied as two coatings. The nails with the special terpolymer-containing formulation applied as two coatings also were somewhat superior with regard to tensile strength and impact absorption.

Tests have also been run that demonstrate the improved strength of thin structures coated with a nail polish embodying the present invention. These tests constituted the coating of eggs with the new nail polish. In such tests eggs of the same size and apparent quality had their blunt halves (halves including the blunt ends) similarly coated with two coats of the new nail polish. The eggs then were suspended from strings attached to girdles secured to the eggs at the mid-point of their longitudinal axes. A similar number of like eggs were suspended from strings but were not coated. The strings were attached at their free ends to a high point 80 centimeters from the centers of the eggs. The eggs were swung from the suspension point 38 centimeters to opposite sides of the point with their blunt ends facing each other. The eggs were paired. One egg in each instance had the double coat of the new nail polish and the other egg was uncoated. The eggs then were released, having been so held that upon their release they would swing blunt end foremost. The lengths of the strings were adjusted so that the centers of the blunt ends would strike each other. In 80% of the tests the uncoated eggs broke. In 20% of the tests the coated eggs broke. That the coated eggs ever broke was due to the fact that eggs are a product of nature and, although in the tests they were selected to be as like as they could be, the thickness of the shells could not be determined without destruction. 80% vs. 20% is statistically significant and shows the substantial superiority of a thin shaped sheet which has been coated with the new nail polish over a similar sheet which has not been coated.

It thus will be seen that there is provided a nail polish which achieves the various objects of the invention and which is well adapted to meet the conditions of practical use.

As various possible embodiments might be made of the above invention, and as various changes might be made in the embodiment above set forth, it is to be understood that all matter herein described is to be interpreted as illustrative and not in a limiting sense.

Having thus described the invention, there is claimed as new and desired to be secured by Letters Patent:

1. A liquid nail polish for application to nails on a human, said nail polish constituting a composition essentially consisting of:
   (A) nitrocellulose,
   (B) a mixture of solvents for nitrocellulose comprising ethyl acetate, butyl acetate, toluene and butyl alcohol,
   (C) a terpolymer of
      (i) laurolactam,
      (ii) caprolactam, and
      (iii) hexamethylene diamine adipate,
      (iv) in equimolecular proportions,
   (D) a solvent for said terpolyer, comprising trichloroethane and ethyl alcohol,
   (E) the nitrocellulose and the terpolymer being dissolved in the solvents for the nitrocellulose and for the said terpolymer,
   (F) the dissolved terpolymer initially being of a particle size less than 80 microns,
   (G) said dissolved terpolymer being present in an amount in the nail polish of from between 0.001% to 0.1% by weight of the composition which is effective to impart to the nails an improved flexural strength when the composition is applied as a coating thereon and permitted to dry.

2. A liquid nail polish as set forth in claim 1 which further includes about 7% to about 10% of toluene-sulfonamide-formadehyde resin.

* * * * *